(12) United States Patent
Uehara et al.

(10) Patent No.: US 11,857,596 B2
(45) Date of Patent: Jan. 2, 2024

(54) ANIMAL FEED ADDITIVE AND ANIMAL FEED

(71) Applicant: AJINOMOTO CO., INC., Tokyo (JP)

(72) Inventors: Akinori Uehara, Kawasaki (JP);
Kazuki Nakagawa, Kawasaki (JP);
Mayumi Maekawa, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 268 days.

(21) Appl. No.: 17/021,113

(22) Filed: Sep. 15, 2020

(65) Prior Publication Data
US 2021/0000913 A1   Jan. 7, 2021

Related U.S. Application Data

(63) Continuation of application No. PCT/JP2019/011162, filed on Mar. 18, 2019.

(30) Foreign Application Priority Data

Mar. 16, 2018   (JP) ................. 2018-049060

(51) Int. Cl.
*A61K 35/744*   (2015.01)
*A61K 38/12*   (2006.01)
*A23K 20/142*   (2016.01)
*A23K 20/195*   (2016.01)
*A23K 20/26*   (2016.01)
(Continued)

(52) U.S. Cl.
CPC .............. *A61K 38/12* (2013.01); *A23K 10/16* (2016.05); *A23K 20/111* (2016.05); *A23K 20/142* (2016.05); *A23K 20/195* (2016.05); *A23K 20/26* (2016.05); *A23K 40/30* (2016.05); *A23K 50/75* (2016.05); *A61K 31/198* (2013.01); *A61K 31/405* (2013.01); *A61K 31/683* (2013.01); *A61K 35/747* (2013.01); *A61K 47/22* (2013.01);
(Continued)

(58) Field of Classification Search
CPC .................................................. A61K 35/744
See application file for complete search history.

(56) References Cited

U.S. PATENT DOCUMENTS

2005/0266050 A1   12/2005   Smith et al.
2011/0014178 A1   1/2011   Smith et al.
(Continued)

FOREIGN PATENT DOCUMENTS

CN   102404996 A   4/2012
CN   106173265 A   12/2016
(Continued)

OTHER PUBLICATIONS

Chopra et al., "Sonorensin: a new bacteriocin with potential of an anti-biofilm agent and a food biopreservative," Nature, Scientific Reports, 5(13412):1-13, 2015.*
(Continued)

*Primary Examiner* — Rosanne Kosson
(74) *Attorney, Agent, or Firm* — Oblon, McClelland, Maier & Neustadt, L.L.P.

(57) ABSTRACT

The present invention provides a coated-type feed additive composition for improving body weight gain of livestock or feed conversion ratio for livestock comprising: a core containing a physiologically active substance having a property of strengthening a membrane of intestinal epithelial cells; and a core coating agent.

15 Claims, 8 Drawing Sheets

(51) Int. Cl.

| | |
|---|---|
| *A23K 40/30* | (2016.01) |
| *A23K 50/75* | (2016.01) |
| *A23K 10/16* | (2016.01) |
| *A23K 20/111* | (2016.01) |
| *A61K 31/198* | (2006.01) |
| *A61K 31/405* | (2006.01) |
| *A61K 31/683* | (2006.01) |
| *A61K 35/747* | (2015.01) |
| *A61K 47/22* | (2006.01) |
| *A61K 47/44* | (2017.01) |

(52) U.S. Cl.
CPC ........ *A61K 47/44* (2013.01); *A23V 2400/157* (2023.08); *A23V 2400/169* (2023.08)

(56) References Cited

U.S. PATENT DOCUMENTS

| | | |
|---|---|---|
| 2011/0312061 A1 | 12/2011 | Kim et al. |
| 2016/0367608 A1 | 12/2016 | Kim et al. |
| 2019/0008890 A1 | 1/2019 | Bruggeman et al. |

FOREIGN PATENT DOCUMENTS

| | | | |
|---|---|---|---|
| EP | 0 940 088 A2 | 9/1999 | |
| EP | 2 077 076 A1 | 7/2009 | |
| JP | 63-317053 A | 12/1988 | |
| JP | 10-113129 A | 5/1998 | |
| JP | 2009-82149 A | 4/2009 | |
| JP | 2012-510291 A | 5/2012 | |
| JP | 2015-186445 A | 10/2015 | |
| WO | WO 2004/003188 A2 | 1/2004 | |
| WO | WO 2004/026334 A1 | 4/2004 | |
| WO | WO-2005075385 A2 * | 8/2005 | ........... A23K 20/147 |
| WO | WO 2006/016595 A1 | 2/2006 | |
| WO | WO-2007031481 A1 * | 3/2007 | ........... A23K 20/189 |
| WO | WO-2010066397 A1 * | 6/2010 | ........... A23K 20/105 |
| WO | WO 2010/117255 A1 | 10/2010 | |
| WO | WO 2016/118840 A1 | 7/2016 | |
| WO | WO 2017/009257 A2 | 1/2017 | |
| WO | WO-2017182347 A1 * | 10/2017 | ........... A23L 33/135 |

OTHER PUBLICATIONS

English machine translation of Iwanami et al., JP 2668880 B2, 1997.*

Kumaree et al., "Bioencapsulation and application of Lactobacillus plantarum isolated from catfish gut as an antimicrobial agent and additive in fish feed pellets," Ann Microbiol 65:1439-1445, 2015.*

International Search Report dated Jun. 18, 2019 in PCT/JP2019/011162 filed Mar. 18, 2019, 2 pages.

Liu. Y-Y. et al., "Emergence of plasmid-mediated colistin resistance mechanism MCR-1 in animal and human beings in China a microbiological and molecular biological study," Lancet Infect. Di., vol. 16, 2016, 8 pages.

O'Neill, J., "Tackling Drug-Resistant Infections Globally: Final Report and Recommendations," Review on Antimicrobial Resistance, May 2016, 84 pages.

Józefiak, D. et al., "Dietary Nisin Modulates the Gastrointestinal Microbial Ecology and Enchances Growth Performance of the Broiler Chickens," PLOS One, vol. 8, No. 12, Dec. 2013, 12 pages.

Goliomytis, M. et al., "The effects of quercetin dietary supplementation on broiler growth performance, meat quality, and oxidative stability," Poultry Science, vol. 93, No. 8, 2014, 6 pages.

Niewold, T. A., "The Nonantibiotic Anti-Inflammatory Effect of Antimicrobial Growth Promoters, the Real Mode of Action? A Hypothesis," Poultry Science, vol. 86, 2007, 5 pages.

Extended European Search Report dated Oct. 25, 2021 in corresponding European Patent Application No. 19767918.6, 9 pages.

Official Action/Search Report dated Aug. 16, 2023, in corresponding Chinese Patent Application No. 201980019680.2 (with English translation).

* cited by examiner

ANIMAL FEED ADDITIVE AND ANIMAL FEED

TECHNICAL FIELD

The present invention relates to a feed additive suitable for livestock, particularly monogastric animals, and a feed containing the additive.

BACKGROUND ART

According to the United Nations' report "The State of World Population," the world population is estimated to have reached 7 billion in 2011, and is expected to increase to 9.8 billion by 2050. Along with this, the food crisis problem has become more serious, and the demand for meat production has been rapidly increasing, especially in BRICS. Therefore, a technique for improving the productivity of livestock meat is essential.

One of the techniques for improving the productivity of livestock animals is the antibiotic growth promoter (AGP). Antibiotics were originally developed for therapeutic use centered on inhibiting the growth of pathogenic bacteria, such as penicillin, and are widely used as pharmaceuticals. Since then, the use of antibiotics has expanded, and from the latter half of the 1950s, the use for the purpose of promoting the growth of livestock animals has become widespread. On the other hand, in view of the problem of antibiotic resistant bacteria and environmental pollution, its use as a growth promoter in Europe was banned in 2006, and the tightening of regulations was confirmed in the US in 2015. In 2016, it was revealed that a colistin-resistant gene was present on the mobile plasmid (Non Patent literature 1). Also, in 2050, antibiotic resistant bacteria will pose a greater risk than cancer, and if this problem is not addressed, the annual mortality rate can surpass that of cancer and reach 10 million, resulting in an international threat (Non Patent Literature 2). Along with this, AGP and therapeutic drugs for both humans and animals, which are also used for treatment in various countries, are risk-judged to be an urgent task for strengthening regulations. In addition, in the US, the fast food market is also planning to offer antibiotic free meat.

Bacteriocins are one of the alternative candidates for AGP. Bacteriocins are a generic term for proteins and peptides produced by bacteria that have antibacterial activity mainly against the same species and related species, and nisin and plantaricin are widely used as food preservatives. However, they are easily decomposed by digestive enzymes, and thus are not used in feed applications. Patent Literature 1 reports a technique of using a lantibiotic such as nisin in combination with a cell wall-dissolving substance such as lysozyme, a sequestering agent such as a chelating agent, and an antibacterial substance such as egg powder, to thereby suppress the growth of enteric pathogenic bacteria and diseases in livestock animals. Non Patent Literature 3 discloses a technique in which a concentrated solution obtained by separating bacteria from nisin-producing bacteria is added as a feed.

Apart from bacteriocins, Non Patent Literature 4 reports that, as a result of adding 500 to 1,000 ppm of quercetin (flavonoid compound) to the feed, the body weight gain effect (also called the body weight gain efficiency) and feed consumption did not increase, and the feed conversion ratio remained almost unchanged or slightly decreased. Patent Literature 2 is a technique in which an esterified pectin or a mixture thereof is contained in a feed, and it deals with inflammatory diseases.

On the other hand, the mechanism of action of AGP, which shows a growth promoting effect even in a small amount, is not clear. There are various opinions about why antibiotics lead to improvement in feed conversion ratio (Non Patent Literature 5).

Hypothesis 1) AGP prevents potential infections and reduces metabolic costs required by the immune system.

Hypothesis 2) AGP controls the intestinal microbiota, and the intestinal bacteria suppress metabolites such as ammonia to promote the growth of host animals.

Hypothesis 3) AGP suppresses the growth of intestinal bacteria and reduces nutrients used by microorganisms.

Hypothesis 4) AGP weakens the digestive tract wall of livestock animals and enhances nutrient absorption.

T. A. Niewold et al. argue the following against those hypotheses: 1) AGP exhibits an antibacterial effect regardless of the animal's livestock species. 2) AGPs with different antibacterial spectra also exhibit the same growth promoting effect. 3) Some therapeutic antibiotics exhibit no growth promoting effect. 4) The concentration of AGP used is less than the minimum inhibitory concentration MIC, and long-term use at a low volume should easily generate resistant bacteria. 5) The effect of an alternative antibacterial substance exhibiting an antibacterial effect is not stable in its effect despite its high antibacterial effect (Non Patent literature 5).

CITATION LIST

Patent Literatures

Patent Literature 1: International Publication No. WO2004/026334
Patent Literature 2: International Publication No. WO2017/009257

Non Patent Literatures

Non Patent Literature 1: Yi-Yun Liu et al, Lancet Infect Dis (2016) vol. 16 161-165
Non Patent Literature 2: Jim O'Neill, Review on Antimicrobial Resistance, May 2016
Non Patent Literature 3: Damian Jozefiak et al, PLoS ONE (2013) vol. 8(12): e85347
Non Patent Literature 4: M. Goliomytis et al, Poult Sci (2014) vol. 93(8): 1957-62
Non Patent Literature 5: T. A. Niewold, Poultry Science (2007) vol. 86: 605-609

SUMMARY OF INVENTION

Problems to be Solved by the Invention

From the above points, since the mechanism of action of AGP is not clear, there is no effective growth promoting substance to replace AGP at present. Therefore, an object of the present invention is to provide a feed additive which can exhibit a body weight gain effect also on healthy livestock and is economical, and a feed containing the additive.

Means for Solution of the Problems

As a result of diligent studies by the present inventors, it has been found that one of the effects when AGP is used at a low concentration is to strengthen the membrane of intestinal epithelial cells. Furthermore, it has been found from the above that, by providing a healthy chicken with a feed coated with a physiologically active substance having the property of strengthening the membrane of intestinal epithelial cells, it is possible to improving the body weight gain effect and feed conversion ratio. This finding was used as a basis to complete the invention of a feed additive which can, when coated, enhance the body weight gain effect of livestock. Specifically, the disclosure provides the following inventions.

1. A coated-type feed additive composition for improving body weight gain of livestock or feed conversion ratio for livestock comprising: a core containing a physiologically active substance having a property of strengthening a membrane of intestinal epithelial cells; and a core coating agent.
2. A coated-type feed additive composition for improving body weight gain of livestock or feed conversion ratio for livestock according to 1 described above, wherein the physiologically active substance contains at least one selected from the group consisting of bacteriocins, polyphenols, amino acids or derivatives thereof, organic acids or derivatives thereof, HSP inducers, antioxidants, and polysaccharides.
3. A coated-type feed additive composition for improving body weight gain of livestock or feed conversion ratio for livestock according to 1 or 2 described above, wherein the physiologically active substance is at least one bacteriocin selected from the group consisting of nisin, subtilin, plantaricin, and gassericin.
4. A coated-type feed additive composition for improving body weight gain of livestock or feed conversion ratio for livestock according to any one of 1 to 3 described above, wherein the physiologically active substance is contained in a culture of a microorganism which produces the substance.
5. A coated-type feed additive composition for improving body weight gain of livestock or feed conversion ratio for livestock according to any one of 1 to 4 described above, wherein the physiologically active substance is contained in a culture of at least one microorganism selected from the group consisting of *Bacillus, Lactococcus, Lactobacillus, Leuconostoc*, and *Pediococcus*.
6. A coated-type feed additive composition for improving body weight gain of livestock or feed conversion ratio for livestock according to 5 described above, wherein the microorganism is *Bacillus subtilis, Lactococcus lactis*, or *Lactobacillus plantarum*.
7. A coated-type feed additive composition for improving body weight gain of livestock or feed conversion ratio for livestock according to 2 described above, wherein the polyphenol is quercetin or tannin.
8. A coated-type feed additive composition for improving body weight gain of livestock or feed conversion ratio for livestock according to 2 described above, wherein the amino acid is at least one selected from the group consisting of glutamine, phenylalanine, tryptophan, valine, and tyrosine.
9. A coated-type feed additive composition for improving body weight gain of livestock or feed conversion ratio for livestock according to 2 described above, wherein the HSP inducer is polyphosphoric acid or a competence and sporulation factor.
10. A coated-type feed additive composition for improving body weight gain of livestock or feed conversion ratio for livestock according to any one of 1 to 9 described above, wherein the coating agent contains at least one selected from the group consisting of hydrogenated vegetable oil, shellac, zein, hydroxypropyl methylcellulose, and maltitol.
11. A coated-type feed additive composition for improving body weight gain of livestock or feed conversion ratio for livestock according to any one of 1 to 10 described above, wherein the physiologically active substance is at least one bacteriocin selected from the group consisting of nisin, subtilin, plantaricin, and gassericin, and the coating agent is hydrogenated rapeseed oil and/or shellac.
12. A coated-type feed additive composition for improving body weight gain of livestock or feed conversion ratio for livestock according to 11 described above, wherein a coating layer formed by the coating agent has a two-layer structure including a layer formed of hydrogenated rapeseed oil and a layer formed of shellac.
13. A coated-type feed additive composition for improving body weight gain of livestock or feed conversion ratio for livestock according to 12 described above, wherein the layer formed of shellac is in contact with the core, and the layer formed of hydrogenated rapeseed oil is formed thereon.
14. A feed comprising: a coated-type feed additive composition for improving body weight gain of livestock or feed conversion ratio for livestock according to any one of 1 to 13 described above.
15. A method of improving a body weight gain effect and feed conversion ratio of livestock, comprising:
    administering to a coated-type feed additive composition for improving body weight gain of livestock or feed conversion ratio for livestock according to any one of 1 to 13 described above or the feed according to 14 described above.

Advantageous Effects of Invention

The coated-type feed additive and feed of the present invention make it possible to provide a feed additive and feed which can exhibit a body weight gain effect also on healthy livestock and is economical. The feed additive and feed of the present invention also exhibit a body weight gain effect even in a small amount.

DESCRIPTION OF EMBODIMENTS

[Core]

Figure 1A:
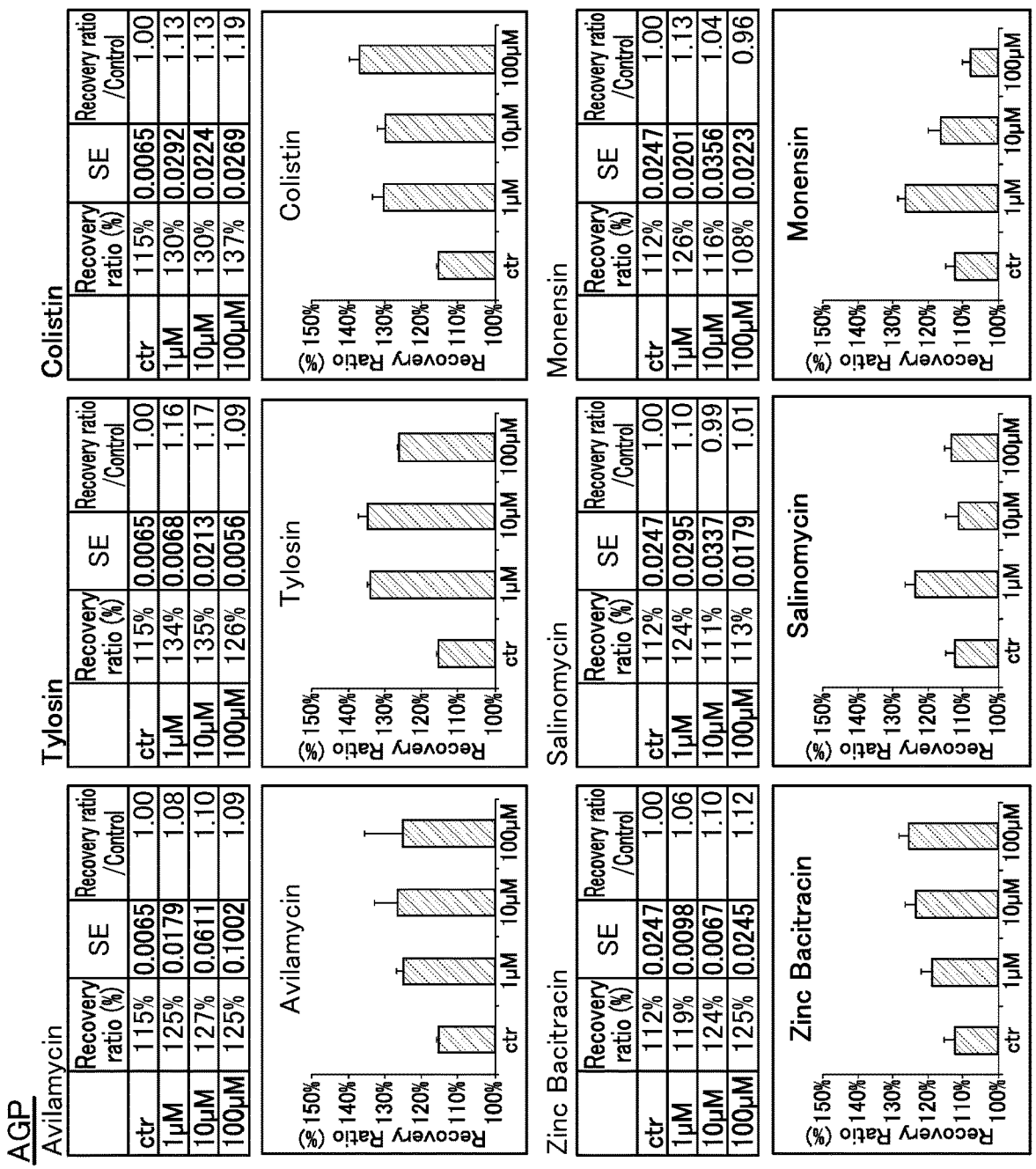
FIG. 1A illustrates the recovery ratio of the barrier function at various concentrations of various physiologically active substances (AGPs) (Experimental Example A).
Figure 1B:
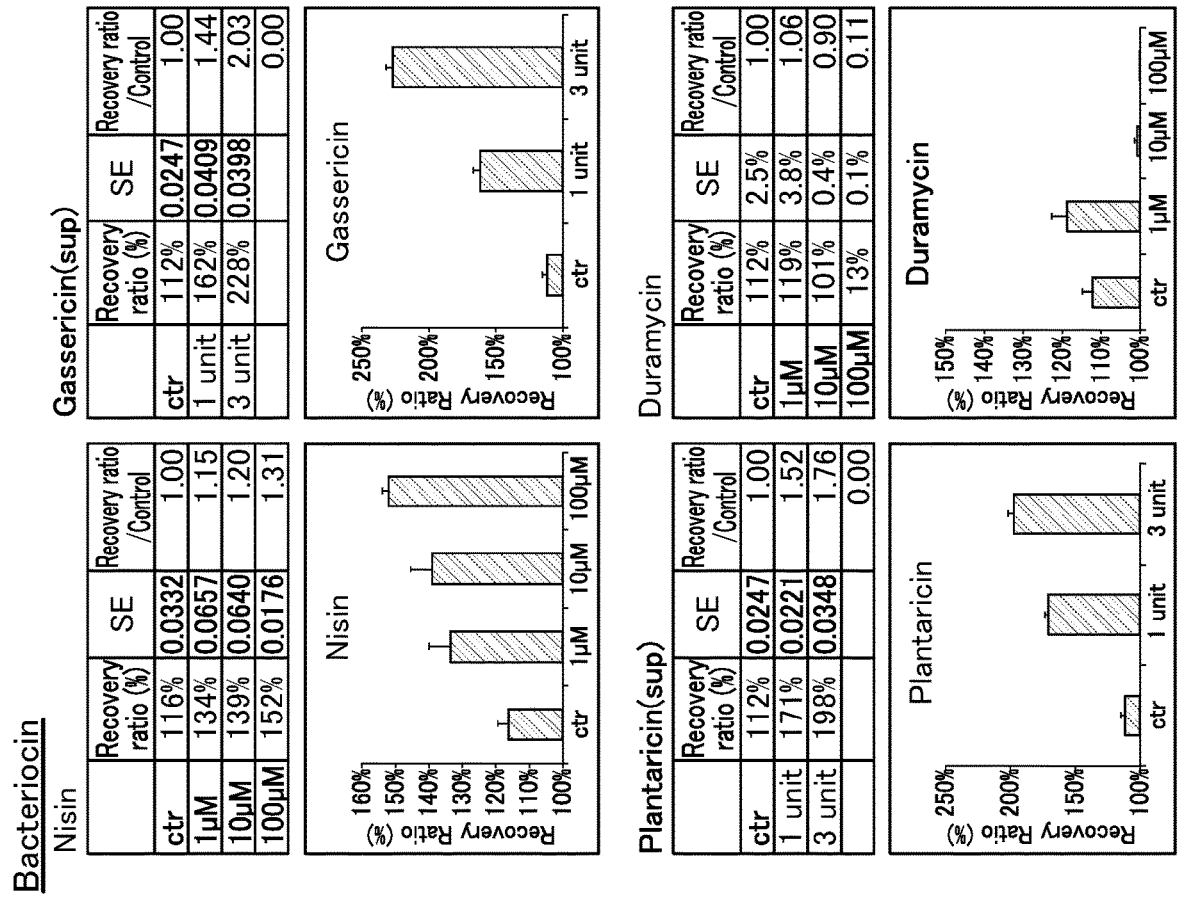
FIG. 1B illustrates the recovery ratio of the barrier function at various concentrations of various physiologically active substances (bacteriocins) (Experimental Example A).
Figure 1C:
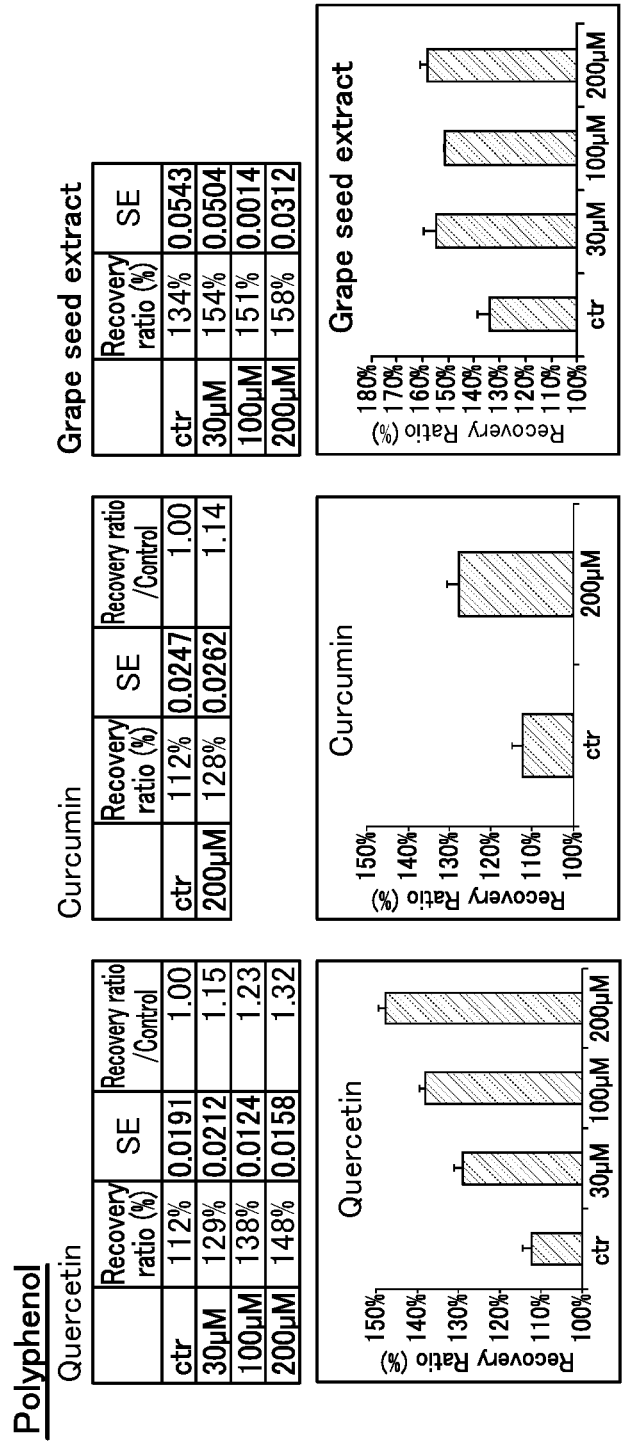
FIG. 1C illustrates the recovery ratio of the barrier function at various concentrations of various physiologically active substances (polyphenols) (Experimental Example A).
Figure 1D:
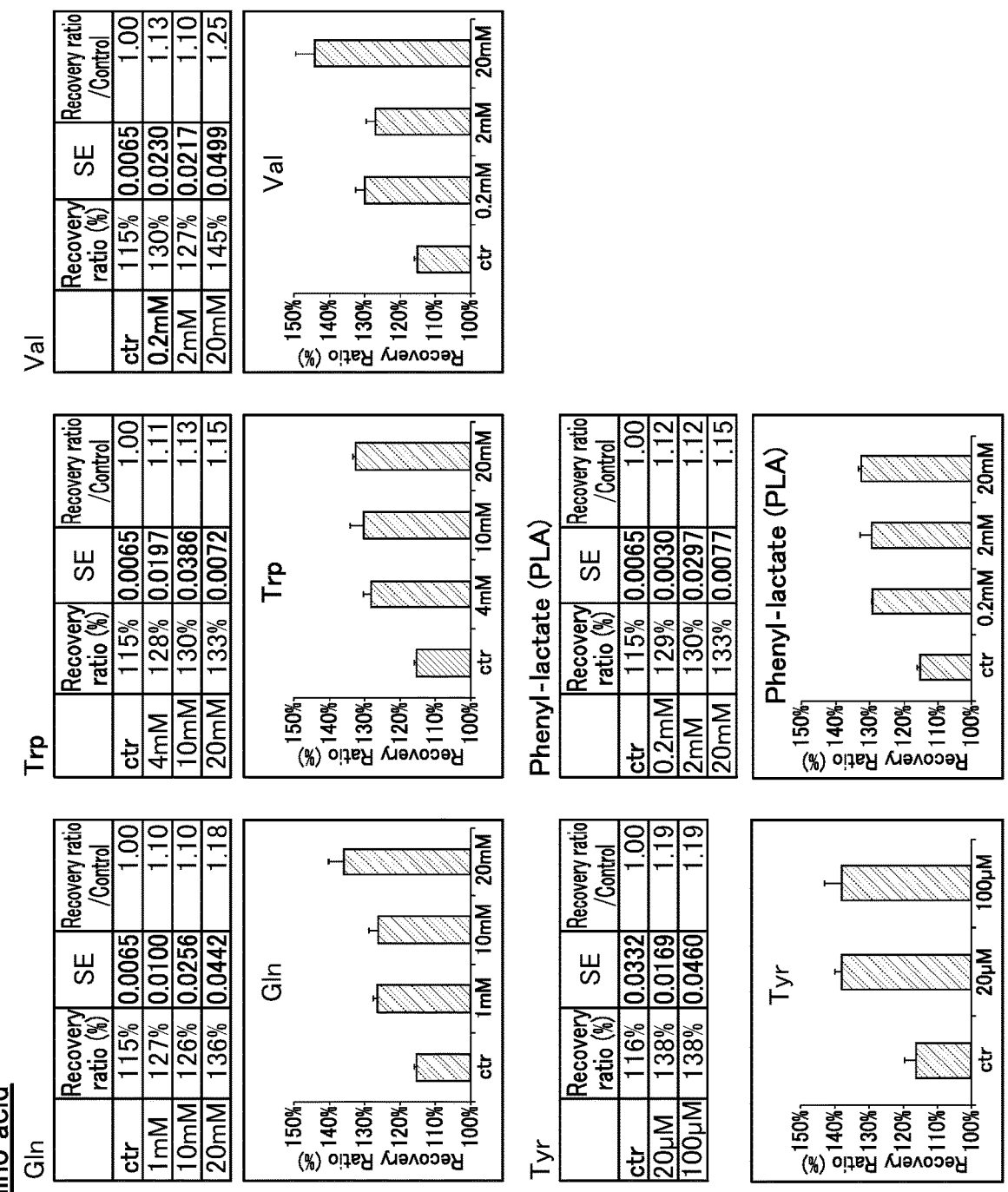
FIG. 1D illustrates the recovery ratio of the barrier function at various concentrations of various physiologically active substances (amino acids) (Experimental Example A).
Figure 1E:
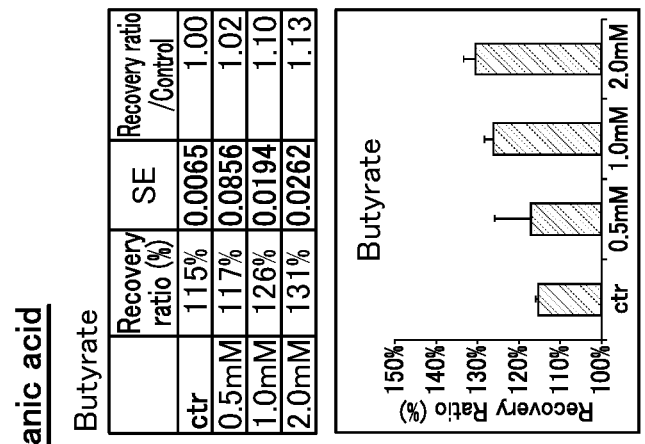
FIG. 1E illustrates the recovery ratio of the barrier function at various concentrations of various physiologically active substances (organic acids) (Experimental Example A).
Figure 1F:
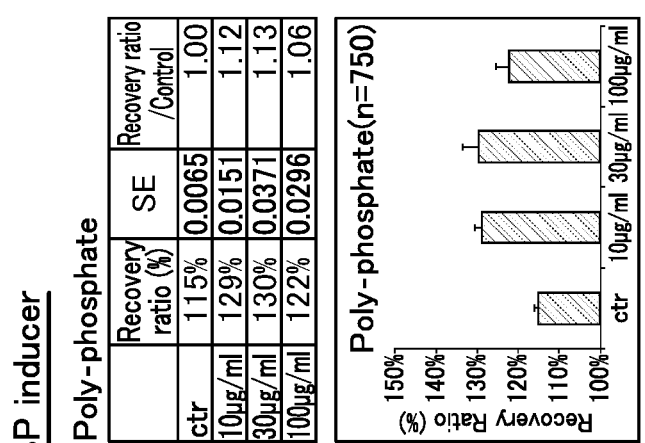
FIG. 1F illustrates the recovery ratio of the barrier function at various concentrations of various physiologically active substances (HSP inducers) (Experimental Example A).
Figure 1G:
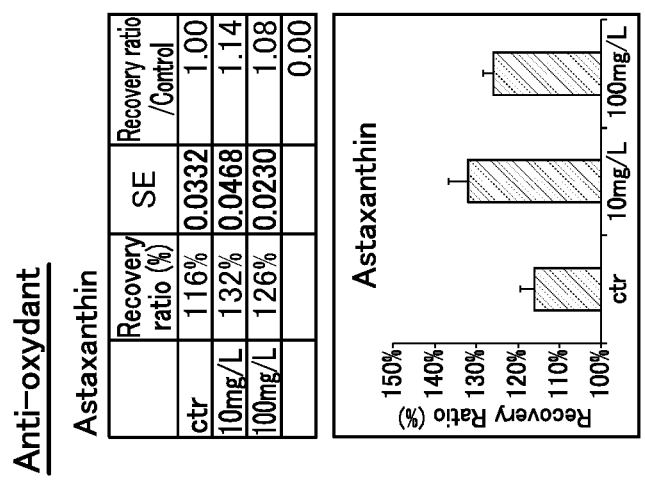
FIG. 1G illustrates the recovery ratio of the barrier function at various concentrations of various physiologically active substances (antioxidants) (Experimental Example A).
Figure 1H:
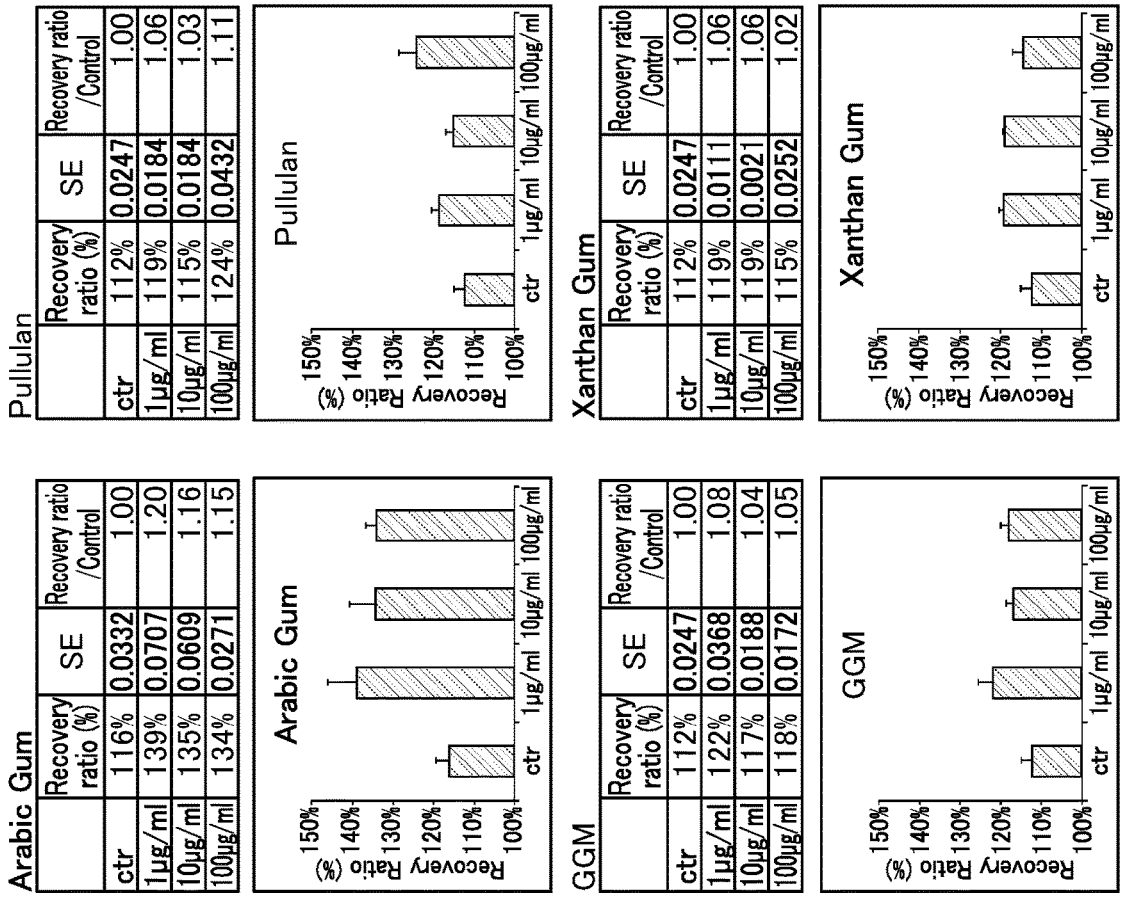
FIG. 1H illustrates the recovery ratio of the barrier function at various concentrations of various physiologically active substances (polysaccharides) (Experimental Example A).

When the present inventors comprehensively investigated physiologically active substances, it was found that at least one selected from the group consisting of bacteriocins, polyphenols, amino acids or derivatives thereof, organic acids or derivatives thereof, heat shock protein (HSP) inducers, antioxidants, and polysaccharides was observed to have an excellent membrane-strengthening ability.

Bacteriocins are classified into two classes, Class I and Class II, according to the classification of Paul D. Cotter (Nat. Rev. Microbiol. 2005 Volume 3 (10), pp 777-88).

Bacteriocins belonging to Class I are also called lantibiotics, and their structure has an abnormal amino acid generated by post-translational modification. Specific examples include nisin A, nisin Z, nisin Q, subtilin, duramycin, mersacidin, and lactisin-481.

Class II are peptides containing no abnormal amino acids in their structure. Class II is further classified into three subclasses a to c. Specific examples of bacteriocins belonging to Class IIa include pediocin PA-1 and enterocin A. It is known that bacteriocins belonging to Class IIb are two peptides produced at the same time, and they synergistically enhance the effects of each other. Specific examples include plantaricin (PlnE, PlnF), enterocin X (Xalpha, Xbeta), and lactococcin Q (Qalpha, Qbeta). Bacteriocins belonging to Class IIc have a cyclic structure in which the N-terminal and C-terminal are linked via a peptide bond. Specific examples include gassericin A, circularin A, and lactocyclicin Q.

The bacteriocin used in the present invention is preferably bacteriocin belonging to Class I, Class IIb, and Class IIc. The bacteriocin used in the present invention is more preferably nisin, gassericin, plantaricin, and subtilin.

Note that, when no alphabetical letter is attached after the name of each bacteriocin, it means the generic name of that bacteriocin (for example, the term "nisin" is a concept including nisin A, nisin Z, and the like).

The experiments of the present inventors observed a membrane-strengthening ability in nisin, so that the index for screening bacteriocin having a membrane-strengthening ability was examined, and it was found that the membrane-strengthening ability was not necessarily correlated with the antibacterial activity or antibacterial spectrum (see Experimental Example B described later).

It is known that the antibiotics used as AGP are not decomposed by digestive enzymes, so that the activity continues even in the body and that they have antibacterial activity even after excreted as feces. On the other hand, bacteriocin, which is a protein or peptide, is easily decomposed by digestive enzymes, so that its activity is lost in the digestive tract. When used in feed applications, it is desirable to protect (coat) it so that it will not be inactivated by digestive enzymes. If protected, 10 to 100 ppm in the small intestine will exhibit sufficient membrane-strengthening ability. After that, the bacteriocin transferred to the feces is safe because it is inactivated by the enzymes in the feces. Therefore, even when a feed additive or feed containing bacteriocin instead of AGP is administered to livestock, there is an advantage that the problem of antibiotic resistant bacteria does not occur. Note that, in the present specification, "ppm" means "ppm by mass."

The polyphenol used in the present invention is quercetin, curcumin, and the like, and quercetin is preferable.

The amino acid used in the present invention is glutamine (Gln), tryptophan (Trp), valine (Val), tyrosine (Tyr), phenylalanine (Phe), and the like. The amino acid derivative is phenyl lactatic acid (PLA) and the like.

The organic acid used in the present invention is butyric acid and the like. The organic acid has a total of about 2 to 5 carbon atoms. The organic acid derivative is, for example, an ester with an alcohol having 1 to 5 carbon atoms.

The HSP inducer (heat shock protein (HSP) inducer) used in the present invention is polyphosphate and a sporulation factor (competence and sporulation factor (CSF)) derived from *Bacillus subtilis*.

The antioxidant used in the present invention is astaxanthin and the like.

The polysaccharide used in the present invention is gum arabic, pullulan, galactoglucomannan (GGM), xanthan gum (XG), and the like.

In the present invention, the physiologically active substances may be used alone or in combination of two or more kinds. The physiologically active substance used in the present invention is preferably a bacteriocin, a polysaccharide, an amino acid, or a combination thereof, and more preferably nisin, Tyr, or a combination thereof.

Note here that it is known polyphosphoric acid strengthens the barrier function by increasing the productivity of heat shock protein (HSP inducer) (Shuichi Segawa et. al., PLoS ONE, 2011, 6(8): e23278). Induction of stress response proteins typified by heat shock proteins is believed to strengthen the intercellular barrier function.

Meanwhile, the tight junction is a layer which is formed by the cell membranes of adjacent cells adhering to each other with their outer membrane fused to each other, and is located at the boundary between the basolateral membrane and the apical membrane of epithelial cells, and is considered to prevent the membrane proteins and lipids from intermingling between them (Iwanami "Seibutugaku Jiten," Fourth Edition, CD-ROM Version, 1998).

Without wishing to be bound by any theory, it is presumed that the physiologically active substance used in the present invention has a membrane-strengthening ability due to one or both of the function of preventing substance diffusion by the tight junction and the intercellular barrier function by the stress response protein. It was considered that strengthening the tight junction would lead to health, but there was no feed that could allow a substance capable of strengthen the tight junction to reach the intestines. In addition, it was not known that an antibacterial agent capable of strengthening the tight junction in vitro exhibited a body weight gain effect when administered to livestock.

The purity of the physiologically active substance used in the present invention is not limited as long as the desired effect is obtained. For example, a physiologically active substance obtained by being produced by a microorganism can be used together with the culture. The solid content in the fermentation broth can be obtained by freeze-drying, or the fermentation broth can be obtained as a solid content by spray granulation.

Alternatively, as the physiologically active substance used in the present invention, a secreted product or extracted product from plants, algae, crustaceans, or fish can be used as it is. As the physiologically active substance used in the present invention, a commercially available product can be used as it is.

Among the physiologically active substances, plants containing polyphenols include grapes, wine, tea, apples, blueberries, persimmons, bananas, turmeric, cinnamon, coffee beans, citrus fruits, onions, and the like.

As a microorganism that produces polysaccharides among physiologically active substances, for example, galactoglucomannan (GGM) produced by *Lipomyces starkeyi* can be obtained by the methods described in Japanese Patent Application Publication No. Hei 7-298873 and Japanese Patent Application Publication No. Hei 9-131199. Microorganisms that produce polysaccharides among physiologically active substances include *Xanthomonas campestris*, *Aureobasidium pullulans*, *Lipomyces Starkeyi*, Phaeophyta as brown algae, and Eucheuma as algae. In addition, the cases of plants include gum arabic (*Acacia senegal*), guar beans (*Cyamopsis tetragonoloba*), ibaranori (*Hypnea musciformis*), cod (*Tara spinosa*), locust beans (*Ceratonia siliqua*), and the like.

Among the physiologically active substances, microorganisms that produce amino acids or derivatives thereof include *Brevibacterium flavum*, *Corynebacterium glutamicum*, *Bacillus subtilis*, *Escherichia coli*, and the like.

Among the physiologically active substances, microorganisms that produce organic acids or derivatives thereof include *Lactobacillus*, *Bifidobacterium*, *Clostridium*, and the like.

Among the physiologically active substances, microorganisms that produce HSP inducers include *Bacillus*, *Lactococcus lactis*, *Lactobacillus*, *Leuconostoc*, and *Pediococcus*.

Among physiologically active substances, microorganisms that produce antioxidants include *Phaffia rhodozyma* and *Pseudomonas thiazolinophilum*, and *Haematococcus pluvialis* as algae.

Also, bacteriocin, which is one of the physiologically active substances used in the present invention, is preferably a culture product of at least one microorganism selected from the group consisting of *Bacillus*, *Lactococcus*, *Lactobacillus*, *Leuconostoc*, and *Pediococcus*.

In particular, the microorganism that produces bacteriocin is preferably a culture product of *Bacillus subtilis*, *Lactococcus lactis*, *Lactobacillus plantarum*, *Lactobacillus acidophilus*, *Lactobacillus alimentarius*, *Lactobacillus amylolyticus*, *Lactobacillus amylovorus*, *Lactobacillus aviaries*, *Lactobacillus brevis*, *Lactobacillus buchneri* (cattle), *Lactobacillus bulgaricus*, *Lactobacillus casei*, *Lactobacillus cellobiosus*, *Lactobacillus crispatus*, *Lactobacillus curvatus*, *Lactobacillus delbrueckii*, *Lactobacillus farciminis* (swine), *Lactobacillus fermentum*, *Lactobacillus gallinarum*, *Lactobacillus gasseri*, *Lactobacillus helveticus*, *Lactobacillus hilgardii*, *Lactobacillus johnsonii*, *Lactobacillus kefiranofaciens*, *Lactobacillus kefiri*, *Lactobacillus lactis*, *Lactobacillus mucosae*, *Lactobacillus panis*, *Lactobacillus paracasei*, *Lactobacillus paraplantarum*, *Lactobacillus pentosus*, *Lactobacillus pontis*, *Lactobacillus reuteri*, *Lactobacillus rhamnosus*, *Lactobacillus sakei*, *Lactobacillus salivarius*, *Lactobacillus sanfranciscensis*, *Lactobacillus zeae*, *Lactococcus lactis*, *Leuconostoc citreum*, *Leuconostoc lactis*, *Leuconostoc mesenteroides*, *Pediococcus acidilactici*, *Pediococcus cerevisiae/damnosus*, *Pediococcus dextrinicus*, and *Pediococcus pentosaceus*, which are registered with the Association of American Feed Control Officials (AAFCO) or the European Food Safety Authority (EFSA).

In particular, culture products of *Lactococcus lactis*, *Bacillus subtilis*, *Lactococcus lactis*, *Lactobacillus plantarum*, *Lactobacillus gasseri*, and *Clostridium beijerinckii* are preferable. Among these, a culture product of *Lactococcus lactis* is preferable.

Particularly, culture products of *Lactococcus lactis* FERM BP-8552 (nisin Z-producing bacterium), *Bacillus subtilis* ATCC 6633 (subtilin-producing bacterium), *Lactococcus lactis* NCIMB 702054 (nisin Z-producing bacterium), *Lactobacillus plantarum* JCM 1057 (plantaricin-producing bacterium), *Lactobacillus gasseri* LA39 JCM 11657 (gassericin A-producing bacterium), *Clostridium beijerinckii* JCM 1390 (circularin A-producing bacterium) are preferable. *Lactococcus lactis* FERM BP-8552 (nisin Z-producing bacterium) and *Lactococcus lactis* NCIMB 702054 (nisin Z-producing bacterium) are most preferable.

Note that *Lactococcus lactis* FERM BP-8552 was deposited on Nov. 19, 2003 with the International Patent Organism Depositary, the National Institute of Advanced Industrial Science and Technology (postal code 305-8566, 1-1-1 Higashi, Tsukuba, Ibaraki Prefecture, Japan, currently the National Institute of Technology and Evaluation, postal code 292-0818, 2-5-8 Kazusakamatari, Kisarazu, Chiba Prefecture, Japan). In the present specification, this strain may be referred to as AJ110212.

*Bacillus subtilis* ATCC 6633 has been deposited with the American Type Culture Collection, Manassas, VA, USA.

*Lactococcus lactis* NCIMB 702054 has been deposited with the National Collection of Industrial, Food and Marine Bacteria, NCIMB Ltd., Aberdeen, Scotland, UK.

*Lactobacillus plantarum* JCM 1057, *Lactobacillus gasseri* LA39 JCM 11657, and *Clostridium beijerinckii* JCM 1390 have been deposited with Japan Collection of Microorganisms, RIKEN BioResource Research Center (postal code 305-0074, 3-1-1 Koyadai, Tsukuba City, Ibaraki Prefecture).

The core may contain a protective agent. The protective agent includes skim milk, amino acid salts such as sodium glutamate, sugar alcohols such as sorbitol, and disaccharides such as trehalose and sucrose.

The core may contain an excipient. The excipient is not particularly limited as long as it is one commonly used for improving shape formation, and examples thereof include calcium carbonate, silicon dioxide, calcium silicate, zeolite, sorbitol, corn starch, talc, yeast bentonite, rice husk, liquid paraffin, polysaccharides other than polysaccharides having a property of aggregating gram-negative bacteria, monosaccharides, and disaccharides. When the core contains an excipient, the amount of the excipient is usually preferably 0.1 to 100 parts by mass based on 100 parts by mass of the core.

The core may also contain any additives that may be included in conventional feed. When the core contains an optional additive, the amount of the optional additive is usually preferably 0.1 to 100 parts by mass based on 100 parts by mass of the core.

[Coating Agent]

The coating agent is a substance capable of forming an enteric coating and can be used without particular limitation as long as it is a substance safe for livestock to ingest. The coating agent may be used alone or in combination of two or more kinds. From the viewpoint of easy handling and economical efficiency, the coating agent is preferably hydrogenated vegetable oil, or shellacs, zein, hydroxypropyl methylcellulose, maltitol, and the like which are substances commonly used as tablet coating agents. The hydrogenated vegetable oil includes hydrogenated oils of rapeseed oil, linseed oil, safflower oil, sunflower oil, soybean oil, corn oil, peanut oil, cottonseed oil, sesame oil, rice oil, olive oil, palm oil, palm kernel oil, or coconut oil. The coating agent is preferably hydrogenated rapeseed oil and shellac. The layer of hydrogenated rapeseed oil is preferable because it can dissolve the core in a short period of time. The layer of shellac is preferable because it can dissolve the core with neutral to alkaline (after passing the stomach).

Alternatively, the coating agent may be a microorganism itself that produces such a physiologically active substance.

The coating agent is in an amount of preferably 5 to 90% by mass, and more preferably 20 to 30% by mass, based on the total mass of the coated-type feed additive of the present invention. The coating agent may also contain any additives that may be included in conventional feed.

The coating may be a single layer or multiple layers of two or more layers. The multi-layer coating is preferable because it is easier to control the dissolution rate in the body. In particular, it is preferable that the outermost layer is a layer of hydrogenated rapeseed oil and the innermost layer in contact with the core is a layer of shellac, because the coating agent dissolves in the intestine rather than in the stomach.

The dissolution rate of the coated-type feed additive of the present invention in gastric juice is desirably less than 50%, and the difference between the dissolution rate in intestinal juice and the dissolution rate in artificial gastric juice is desirably 10% or more. For the purpose of achieving such a dissolution rate, it can be adjusted by forming a two-layer membrane or a multi-layer membrane, or by controlling the type of coating agent and the membrane thickness for each layer.

[Coating Method]

The method of coating the core is not particularly limited, and for example, it is possible to obtain a coated-type feed additive by spraying a coating agent in a liquid state, heated to a temperature higher than the melting point, while allowing the powdered or granular core to flow with a commercially available fluidized bed spray granulator. The coated-type feed additive obtained from powdered or granular polysaccharides has a size of preferably about 0.05 to 5 mm because handling is easy. In addition, the temperature for heating the coating agent is not particularly limited as long as it is equal to or higher than the melting point of the coating agent, but it is preferably higher than the melting point of the coating agent by about 5° C. to 15° C.

[Feed]

The coated-type feed additive of the present invention can be given to livestock as it is, or can be used as a feed together with an excipient or diluent such as corn, soybean flour, rice bran, fish meal, or brewer's yeast. The feed of the present invention may also contain any additives that may be included in feed. The feed of the present invention is suitable for continuous daily intake. The feed intake varies depending on the size of livestock. For example, in the case of chickens, it is desirable that the physiologically active substance is fed at a daily intake of about 1 to 200 ppm and preferably 10 to 100 ppm, based on the feed other than the coated-type feed additive.

In the present specification, the term "livestock" refers to creatures that are bred by humans Specific examples include ruminants such as cows, sheep, and goats, and monogastric animals such as horses, pigs, chickens, dogs, and fish. It is particularly preferable to give the feed of the present invention to monogastric animals.

The method of feeding the coated-type feed additive of the present invention is not particularly limited.

EXAMPLES

Experimental Example A: Membrane Strengthening Experiment

The membrane-strengthening ability of the test substance was evaluated according to the description in J. Nutr. (2009) volume 139(5), pp 965-974.

Caco-2 cells (human intestinal epithelial cells (ECACC, Code 86010202)) were seeded in a double-layered Transwell system, and cultured in DMEM medium at 37° C. On the 12th day of culture, TNF-α, was added to reduce the barrier function of Tight Junction. On the 14th day of culture, the test substance was added, the mixture was cultured at the same temperature for 24 hours, and then Millicell ERS-2 (manufactured by Millipore) was used to measure the transepithelial electrical resistance value TER ($\Omega$*cm2), thereby evaluating the restoration (recovery ratio %) of the barrier function. FIG. 1A to FIG. 1H present the results.

As illustrated in FIG. 1A, it was confirmed that AGP, such as avilamycin and colistin, had a function of strengthening the barrier function even at a low concentration. With the group added with TNF-α alone used as a control, a recovery ratio/control of 1.1 or more was determined to have the membrane-strengthening ability. Table 1 presents the concentration of the material itself when the recovery ratio/control of each physiologically active substance is around 1.1. Quercetin, grape seed extract (manufactured by Ajinomoto Co., Inc.), nisin A, tyrosine (manufactured by Ajinomoto Co., Inc.), astaxanthin (manufactured by DSM), and the like were also observed to have the function of strengthening the barrier function.

TABLE 1

| Material | Material | conc. | | Recovery ratio/ctr*1 | Recovery ratio (%) |
|---|---|---|---|---|---|
| Antibiotic Growth Promoter (AGP) | Avilamycin | 10 | uM | 1.10 | 127 |
| | Tylosin | 10 | uM | 1.17 | 135 |
| | Colistin | 1 | uM | 1.13 | 130 |
| | Zinc Bacitracin | 10 | uM | 1.10 | 124 |
| | Salinomycin | 1 | uM | 1.10 | 124 |
| | Monensin | 1 | uM | 1.13 | 126 |
| | Enramycin | 100 | uM | 1.28 | 144 |
| Bacteriocin | Nisin (Class I) | 10 | uM | 1.20 | 139 |
| | Duramycin (Class I) | 1 | uM | 1.04 | 120 |
| | Gassericin (sup)*2 (Class IIc) | 1 | unit | 1.44 | 162 |
| | Plantaricin (sup)*3 (Class IIb) | 1 | unit | 1.52 | 171 |

TABLE 1-continued

| Material | Material | conc. | Recovery ratio/ctr*1 | Recovery ratio (%) |
|---|---|---|---|---|
| Polyphenol | Quercetin | 100 uM | 1.23 | 138 |
|  | Curcumin | 200 uM | 1.14 | 128 |
|  | Grape Seed Extract*4 | 200 uM | 1.19 | 157 |
| Amino acid | Glutamine | 20 mM | 1.18 | 136 |
|  | Tryptophan | 4 mM | 1.11 | 128 |
|  | Valine | 0.2 mM | 1.13 | 130 |
|  | Phenyl-lactate | 0.2 mM | 1.12 | 129 |
|  | Tyrosin | 20 uM | 1.19 | 138 |
| Organic acid | Butylate | 2.0 mM | 1.13 | 131 |
| chelate /HSP inducer | Poly-Phosphate (750) | 10 ppm | 1.12 | 129 |
| Anti-oxidant | Astaxanthin | 10 mg/L | 1.14 | 132 |
| Poly Saccharide | Arabic Gum | 1 ppm | 1.20 | 139 |
|  | Pullulan | 100 ppm | 1.11 | 124 |
|  | GGM | 1 ppm | 1.08 | 122 |
|  | XG | 1 ppm | 1.06 | 119 |

*1: Comparison value with Ctr (group added with TNFα alone)
*2: Gassericin (sup): Culture supernatant of the production bacteria (*Lactobacillus gasseri* LA39 JCM 11657) concentrated three times with an ultrafiltration membrane (MW: 3,000)
*3: Plantaricin (sup): Culture supernatant of the production bacteria (*Lactobacillus plantarum* JCM 1057) concentrated three times with an ultrafiltration membrane (MW: 3,000)
*4: "OmniVin™ 10R" manufactured by Ajinomoto

Example 1: Coated-Quercetin

1-1: Preparation of Coated-Quercetin

Quercetin (reagent manufactured by Tokyo Chemical Industry Co., Ltd. (purity 95%)) was used as the core, and hydrogenated rapeseed oil (melting point 67° C.) and natural resin shellac were used as the coating agents. The powdered or granular core was sprayed with a predetermined amount of coating agent, liquefied by heating to a temperature higher than the melting point, to obtain a coated-type feed additive. The coating was carried out by spraying 5 parts by mass of shellac as the first layer (inner layer) and 17 parts by mass of hydrogenated rapeseed oil as the second layer (outer layer), based on 77 parts by mass of the core.

1-2: Acid Resistance and Enteric Test (Artificial Gastric Juice Treatment) To pure water produced using a pure water production device manufactured by Merck Millipore, 0.2 mass % NaCl and 0.2 mass % pepsin (from Porcine stomach Mucosa, 1:5,000, 2,500 unit/mg) were added to adjust the pH to 2, and then the coated-type feed additive prepared in 1-1 above was charged therein, followed by enzyme treatment at 37° C. for 2 hours. The dissolution rate was measured by automatically and continuously measuring the optical density during this period. Note that the "2 hours" assumes the time from when the feed reaches the stomach of the chicken until it passes. (Artificial Intestinal Juice Treatment) After the artificial gastric juice treatment, 0.2% trypsin (from Porcine Pancreas, 1:5,000; 4,500 unit/mg) was added to adjust the pH to 6, followed by enzyme treatment at 37° C. for 2 hours. The dissolution rate was measured by automatically and continuously measuring the optical density during this period. Note that the "2 hours" assumes the time from when the feed reaches the intestine of the chicken until it passes.

For pH adjustment, hydrochloric acid and sodium hydroxide were used. The optical density was measured at OD 660 nm using Biophoto-recorder TVS062CA manufactured by ADVANTEC.

Figure 2:
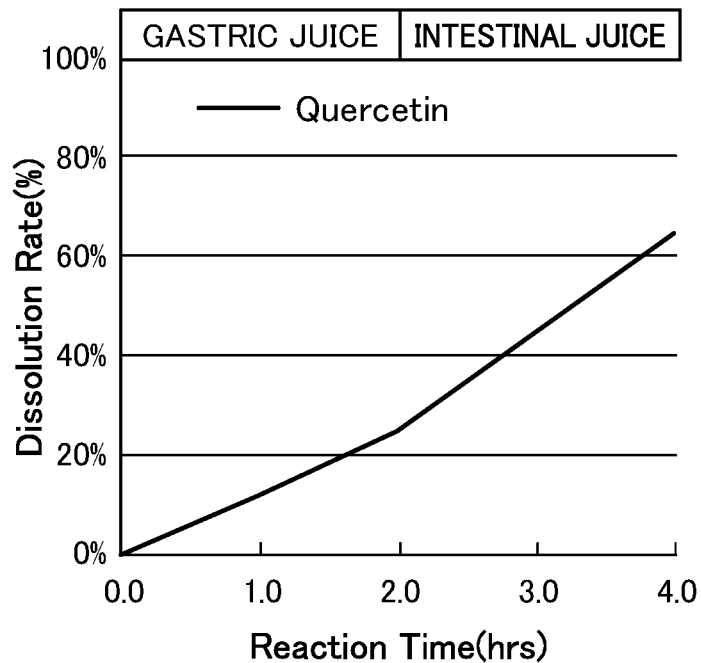
FIG. 2 illustrates the change over time of the dissolution rate of quercetin from the two-layer coated-type feed additive under gastric juice and intestinal juice conditions (1-2 of Examples 1).

FIG. 2 presents the results. From FIG. 2, in the two-layer coating, the dissolution rate within 2 hours from the start of gastric juice treatment was suppressed to 25%, while in the intestinal juice treatment, 65% was dissolved. From these results, it was found that the feed additive having a hydrogenated rapeseed oil layer as the outer layer and a shellac layer as the inner layer had acid resistance and enteric properties, and was excellent in release control.

1-3: Chicken Growth Test

The coated-quercetin prepared by the two-layer coating method of 1-1 above was added to the feed matrix having the composition presented in Table 2 so that the amount of the core agent was 20 ppm and 200 ppm to obtain a feed composition. In a flat poultry house, 25 neonate broiler chickens in 1 section were used, fed with the feed composition, and bred for 22 days at 0 to 21 days of age in triplicate to evaluate the chicken body weight gain (BWG) and feed conversion ratio (FCR=Feed/BWG). Note that a conventional antimicrobial growth promoter (AGP), avilamycin, was used as a positive control. As avilamycin, a commercially available product (Surmax 200 (registered trademark) manufactured by ELANCO, uncoated) was used as it was.

The results are presented with a negative control of 100. Table 3 presents the results. Although it is known that uncoated quercetin has a negative effect on the intestinal microbiota (J. Nutr. 139: 965-974, 2009.), coated-quercetin exhibited a body weight gain effect and feed conversion ratio improvement effect. Note that, since uncoated quercetin has a negative effect on the intestinal microbiota, the chicken growth test using uncoated quercetin was not carried out.

TABLE 2

| Raw Material | Mixing Ratio, Mass % |
|---|---|
| Corn | 45.4 |
| Grain Sorghum | 10.0 |
| Soybean Meal | 30.0 |
| Corn Gluten Meal | 4.00 |
| Fishmeal (CP 65%) | 3.00 |
| L-Lysine Hydrochloride | 0.31 |
| DL-Methionine | 0.35 |
| L-Threonine | 0.12 |
| L-Arginine | 0.16 |
| Animal Oil and/or Fat | 3.49 |
| Dibasic Calcium Phosphate | 1.45 |
| Calcium Carbonate | 1.06 |

TABLE 2-continued

| Raw Material | Mixing Ratio, Mass % |
|---|---|
| Salt | 0.30 |
| Vitamin and Mineral Premix | 0.25 |
| Choline Chloride | 0.02 |
| L-Valine | 0.07 |
| Total | 100 |

*Feed Composition

TABLE 3

| Category | | Addition ppm | 0-3 weeks BWG | FCR |
|---|---|---|---|---|
| AGP | PC1/Avilamycin | 10 | 110% | 96% |
| Membrane Strengthening | Coated Quercetin | 20 | 106% | 98% |
| | Coated Quercetin | 200 | 104% | 98% |

Example 2: Coated-Phe and Coated-Tyr 2-1: Preparation of Coated-Phe and Coated-Tyr Coated-Phe and coated-Tyr were prepared according to the description in 1-1 of Example 1.

2-2: Acid Resistance and Enteric Test

Figure 3:
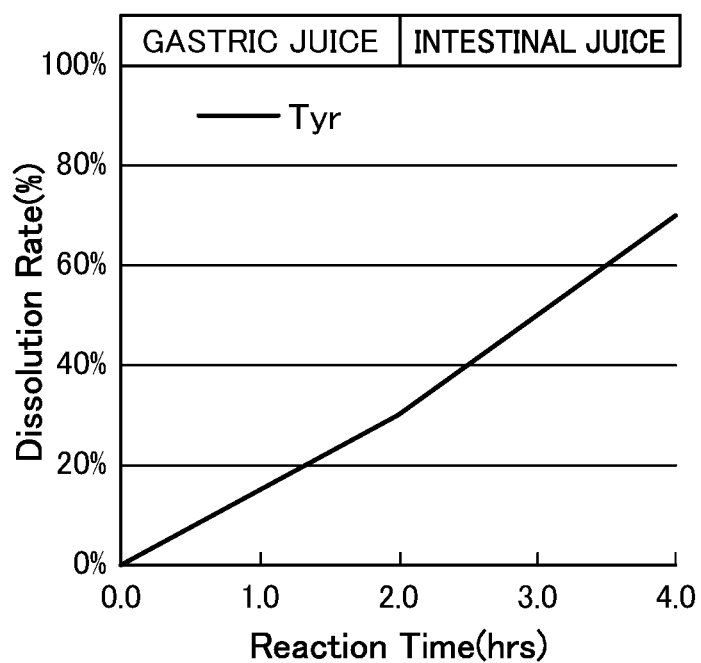
FIG. 3 illustrates the change over time of the dissolution rate of tyrosine from the two-layer coated-type feed additive under gastric juice and intestinal juice conditions (2-2 of Example 2).

The coated-Tyr obtained above was used to carry out acid resistance and enteric test in the same manner as in 1-2 of Example 1. FIG. 3 presents the results.

2-3: Chicken Growth Test

The coated-Phe and coated-Tyr obtained above were added to the feed matrix having the composition presented in Table 2 so that the amount of the core material was 200 ppm, to thereby evaluate the body weight gain effect and feed conversion ratio of chickens according to the method described in 1-3 of Example 1. Table 4 presents the results.

A certain degree of body weight gain effect was confirmed even when Phe and Tyr were not coated, but Phe or Tyr was not detected in the intestinal tract contents or blood as a result of metabolome analysis. It is thus considered that coated-Phe and coated-Tyr are assimilated by intestinal bacteria in feces and rapidly metabolized in blood. Therefore, it is considered that the coated amino acids more stably exhibit the effect than the uncoated amino acids.

TABLE 4

| Category | Addition ppm | 0-3 weeks BWG | FCR |
|---|---|---|---|
| PC1/Avilamycin | 10 | 107% | 95% |
| Phe | 200 | 106% | 98% |
| Coated Phe | 200 | 103% | 97% |
| Tyr | 200 | 104% | 98% |
| Coated Tyr | 200 | 105% | 99% |

2-4: Evaluation of L-Tyr and Coated-L-Tyr by *Salmonella* Infection Test in Chickens The coated-Tyr and Tyr prepared in the same manner as in Example 2-1 were added to the feed matrix having the composition presented in Table 2 so that the amount of the core material was 200 ppm, to thereby prepare a feed. Broilers at 1 day of age were introduced into a breeding facility for infection test (6 broilers/repeat and 2 repeats/test group), then *Salmonella enterica* (SE) was orally administered to the broilers at 2 days of age, and the test feed was fed for 21 days to evaluate the body weight gain effect and feed conversion ratio of chickens. Note that a conventional antimicrobial growth promoter, enramycin, was used as a positive control. As enramycin, a commercially available product ("Enramycin F-80" manufactured by Scientific Feed Laboratory Co., Ltd., uncoated) was used as it was.

The results are presented with a negative control of 100. Table 5 presents the results.

TABLE 5

| Test Group | Addition, ppm | 0-3 week BWG | FCR |
|---|---|---|---|
| Control Group | — | 100% | 100% |
| Enramycin (AGP) | 10 | 107% | 98% |
| L-Tyr | 200 | 96% | 100% |
| Coated-L-Tyr | 200 | 109% | 97% |

As a result, there was no effect in uncoated tyrosine ("L-Tyr"), but coated-Tyr exhibited the same body weight gain effect and feed conversion ratio improvement effect as those of enramycin.

Example 3: Coated-Nisin A 3-1: Preparation of Coated-Nisin A

Nisin A (reagent manufactured by Sigma-Aldrich (nisin content 2.5% by mass, balance sodium chloride and denatured milk solids) was used as the core, and hydrogenated rapeseed oil (melting point 67° C.) and natural resin shellac were used as the coating agents. A coated-type feed additive with a two-layer coating was obtained according to the description in 1-1 of Example 1.

3-2: Acid Resistance and Enteric Test

Figure 4:
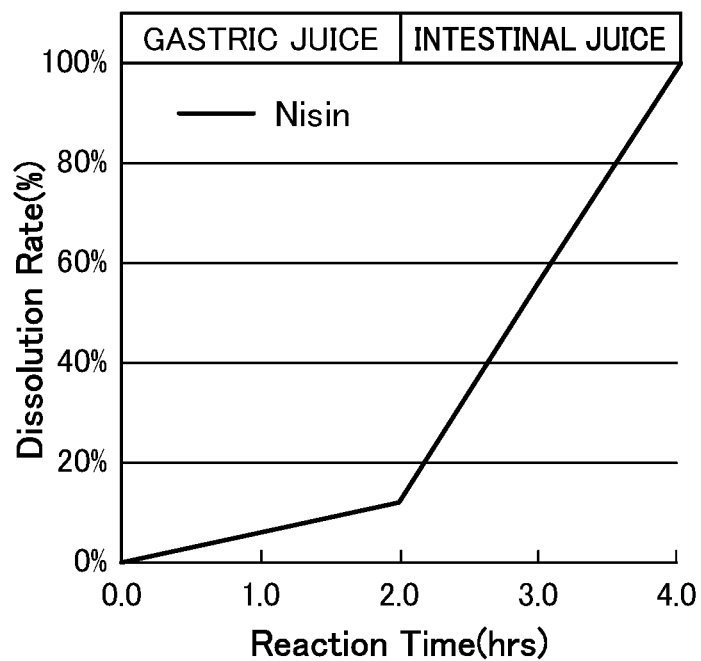
FIG. 4 illustrates the change over time of the dissolution rate of nisin A from the two-layer coated-type feed additive under gastric juice and intestinal juice conditions (3-2 of Example 3).

The coated-nisin A prepared above was used to carry out acid resistance and enteric test in the same manner as in 1-2 of Example 1. FIG. 4 presents the results.

3-3: Chicken Growth Test

The coated-nisin A prepared in 3-1 was added to the feed matrix having the composition presented in Table 2 so that the amount of the core material was 1 ppm and 10 ppm, to thereby evaluate the body weight gain effect and feed conversion ratio of chickens. In a flat poultry house, 25 neonate broiler chickens in 1 section were used, and bred at 0 to 21 days of age in triplicate. Table 6 presents the results. Although nisin decreased in activity by gastric acid and was completely inactivated by the digestive enzyme trypsin, coated-nisin A was observed to have a body weight gain effect and feed conversion ratio improvement effect.

TABLE 6

| Category | Addition (ppm) | 0-3 weeks | |
| --- | --- | --- | --- |
| | | BWG | FCR |
| NC | | 100% | 100% |
| PC1 (W/Avilamycin) | 10 | 104% | 97% |
| PC2 (W/Avilamycin) | 10 | 107% | 94% |
| Coated Nisin A | 10 | 103% | 97% |
| Coated Nisin A | 1 | 101% | 98% |

3-4: Evaluation of Coated-Nisin A and Coated-Pullulan by *Salmonella* Infection Test in Chickens The coated-nisin A prepared in 3-1 was used alone or in combination with coated-pullulan, and added to the feed matrix having the composition presented in Table 2 so that the amount of each core agent added was 10 ppm, to thereby prepare a feed. Broilers at 0 days of age were introduced into a breeding facility for infection test (2 repeats/test group and 6 broilers/repeat), and then *Salmonella enterica* (SE) were administered at 107 counts/broiler with a probe into the crop of the broilers at 2 days of age, and the test feed was fed for 21 days to evaluate the body weight gain effect and feed conversion ratio. Table 7 presents the results.

TABLE 7

| Test Group | Amount Added [ppm] | 0-3 w | |
| --- | --- | --- | --- |
| | | BWG | FCR |
| Control Group | — | 100% | 199% |
| Coated-Nisin A Group | 10 | 102% | 92% |
| Coated-Nisin A + Coated-Pullulan Group | 10, 10 | 105% | 98% |

As a result, both the coated-nisin group and the coated-nisin+coated-pullulan group exhibited a body weight gain effect and feed conversion ratio improvement effect.

3-5: Evaluation of Nisin A and Coated-Nisin A by *Salmonella* Infection Test in Chickens The coated-nisin A and nisin A prepared in the same manner as in Example 3-1 were added to the feed as presented in Table 2 to prepare a feed. Broilers at 0 days of age were introduced into a breeding facility for infection test (6 broilers/repeat and 2 repeats/test group), then *Salmonella enterica* (SE) was orally administered to the broilers at 2 days of age, and the test feed was fed for 21 days to evaluate the body weight gain effect and feed conversion ratio. Note that a conventional antimicrobial growth promoter, enramycin, was used as a positive control. As enramycin, a commercially available product ("Enramycin F-80" manufactured by Scientific Feed Laboratory Co., Ltd., uncoated) was used as it was.

Table 8 presents the results.

TABLE 8

| Test Group | Volume, ppm | 0-3 week | |
| --- | --- | --- | --- |
| | | BWG | FCR |
| Control Group | — | 100% | 100% |
| Enramycin (AGP) | 10 | 107% | 98% |
| Nisin A | 10 | 101% | 100% |
| Coated-Nisin A | 10 | 107% | 97% |

As a result, there was no effect in uncoated nisin A, but coated-nisin A exhibited the same body weight gain effect and feed conversion ratio improvement effect as those of enramycin.

Experimental Example B: Evaluation of Antibacterial Activity and Evaluation of Antibacterial Spectrum for Bacteriocin B-1: Measurement of Minimum Inhibitory Concentration The minimum inhibitory concentrations of AGP and nisin were measured and compared.

*Lactococcus* lactic AJ110212 (FERM BP-8552) was used as the nisin Z-producing bacterium. The nisin Z-producing bacteria were cultured at 100 rpm at 30° C. in a medium (1 L of Lactobacilli MRS Broth manufactured by BD Difco) in a 5 L Sakaguchi flask. The culture was carried out for 20 hours as a standard, and the culture solution was prepared by measuring the optical density at a wavelength of 610 nm with a spectrophotometer (Biophoto-recorder TVS062CA manufactured by ADVANTEC) to be 0.1 or more when diluted 26 times. The obtained culture solution was centrifuged (6,000 G×10 min, 4° C.) to separate a cell fraction (wet cells).

The following strains were used as test bacteria. The medium and culture temperature are written in parentheses at the end of the strain. The MRS medium used was Lactobacilli MRS Broth manufactured by Difco, the GAM medium and LB medium used were manufactured by Nissui Pharmaceutical Co., Ltd., and the NB medium used was manufactured by Difco.

Gram-Positive Bacteria
  *Lactobacillus acidophilus* AJ13778 (MRS, 37° C., corresponding to that deposited at accession number JCM 1132)
  *Lactobacillus salivarius* AJ110152 (MRS, 37° C., corresponding to that deposited at accession number JCM 1231)
  *Bifidobacterium thermophilum* AJ110569 (GAM, 37° C., corresponding to that deposited at accession number JCM 1207)
  *Bacteroides fragilis* JCM 11019 (GAM, 37° C.)
  *Escherichia coli* MG1655 (LB, 37° C., corresponding to that deposited at accession number ATCC 700926)
  *Clostridium perfringens* AJ3350 (GAM, 37° C., corresponding to that deposited at accession number ATCC 10873)

Gram-Negative Bacteria
  *Enterococcus faecalis* AJ110149 (MRS, 30° C., corresponding to that deposited at accession number JCM 5803)
  *Salmonella enterica* AJ2785 (NB, 37° C., corresponding to that deposited at accession number IAM 1648)

Note that the depositary institution for bacteria identified by an accession number starting with JCM is Japan Collection of Microorganisms, RIKEN BioResource Research Center (postal code 305-0074, 3-1-1 Koyadai, Tsukuba City, Ibaraki Prefecture). The depositary institution for bacteria identified by an accession number starting with ATCC is the American Type Culture Collection, Manassas, VA, USA. The depositary institution for bacteria identified by an accession number starting with IAM is IAM Culture Collection, Center for Cellular and Molecular Research, Institute of Molecular and Cellular Biosciences, The University of Tokyo, Tokyo, Japan (collection transferred to JCM).

The minimum inhibitory concentration was calculated by measuring the antibacterial activity by the spot-on-lawn method described in Mayr-Harting, A. et al., Methods Microbiol. 1972, 7A, pp 315-422. In the case of using a culture solution, a qualitative judgment was made based on the size of the inhibition circle. Table 9 presents the results.

TABLE 9

Comparative data on the minimum inhibitory concentrations of AGP and nisin
Minimum inhibitory concentration (mg/mL)

| | Antibiotic Growth Promotor (AGP) | | | | | | | Class IV | |
|---|---|---|---|---|---|---|---|---|---|
| | Class I | | Class III | | | | | | |
| | Polyether-Based, | | | | Macrolide- | Others | | Polypeptide- | Alternative |
| | Ionophore | | Polypeptide-Based | | Based | Chlortetra- | Avila- | Based | to AGP |
| Indicator strain | Salinomycin | Monensin | Bacitracin | Enramycin | Tylosin | cycline | mycin | Colistin | Nisin |
| *Lactobacillus acidophilus* AJ13778 | 2 | 2 | 32 | 0.5 | 1 | 4 | 16 | >100 | 3.1 |
| *Lactobacillus salivarius* AJ110152 | 1 | 1 | 32 | 0.5 | 1 | 3 | 8 | >100 | 1.6 |
| *Clostridium perfringens* AJ3350 | 1 | 1 | 150 | 1 | 4 | 0.062 | 1 | >100 | 1.6 |
| *Enterococcus faecalis* AJ110149 | 0.5 | 2 | 128 | 4 | 4 | ND | 2 | >100 | 3.1 |
| *Escherichia coli* MG1665 | >100 | >100 | >100 | >100 | >100 | 50 | >100 | 4 | >25 |
| *Bacteroides fragilis* JCM11019 | 64 | 128 | >100 | 64 | 4 | 4 | 8 | >100 | 3.1 |
| *Bifidobacterium thermophilum* AJ110569 | 2 | 2 | 4 | 0.5 | 0.01 | 16 | 16 | 128 | 1.6 |
| *Salmonella enterica* AJ2785 | >100 | >100 | >100 | >100 | >100 | 50 | >100 | >100 | >25 |

"ND": indicates no effect detected (not detected).

B-2: Measurement of Antibacterial Spectrum

For compounds difficult to obtain with reagents, the following producing bacteria were cultured in Lactobacilli MRS Broth medium manufactured by Difco at 30° C. to prepare a bacteriocin-containing culture solution.

As bacteriocin/class I: nisin, nisin A used in 3-1 of Example 3 and nisin Z (producing bacteria were *Lactococcus lactis* NCIMB 702054) were used. As the subtilin-producing bacteria, *Bacillus subtilis* ATCC 6633 was used. As duramycin, a reagent manufactured by Sigma-Aldrich (1 mg/ml) was used.

As bacteriocin/class IIb: plantaricin-producing bacteria, *Lactobacillus plantarum* JCM 1057 was used.

As bacteriocin/class IIc: gassericin A-producing bacteria, *Lactobacillus gasseri* LA39 JCM 11657 was used, and circularin A-producing bacteria used was *Clostridium beijerinckii* JCM 1390.

The antibacterial spectrum was evaluated by the spot-on lawn method using a 10-fold concentrated culture solution supernatant. Table 10 presents the results of the investigation.

TABLE 10

Antibacterial Spectrum of Bacteriocin

| | Class I | | | | Class IIb | Class IIc | |
|---|---|---|---|---|---|---|---|
| Indicator Strain | Nisin A* | Nisin Z | Subtilin | Duramycin* | Planta-ricin | Gassericin A | Circularin A |
| *Clostridium perfringens* | +++++ | +++ | + | +++++ | ++ | ND | ND |
| *Lactobacillus acidophilus* | ++++ | +++ | + | + | +++ | + | + |
| *Lactobacillus salivarius* AJ110152 | +++++ | ++++ | + | ND | + | ND | ND |
| *Bifidobacterium thermophilum* AJ110569 | +++++ | ++++ | + | ++ | + | + | + |
| *Bacteroides fragilis* JCM11019 | ++++ | + | ND | + | + | + | + |
| *Escherichia coli* MG1655 | ++ | ND | ND | ND | ND | ND | ND |
| *Enterococcus faecalis* AJ110149 | +++++ | +++ | + | ND | ++ | ND | ND |

Nisin A (1 mg/ml), Duramycin (1 mg/ml), Others: Bacteriocin producers
"+" to "++++": indicates the strength of antibacterial effect. The more "+", the stronger the effect.
"ND": indicates no effect detected (not detected).

From the comparison between Table 9 and Table 10 and Table 1, it was found that the membrane-strengthening function was unrelated to the presence or absence of antibacterial activity and its strength.

Example 4: Coated-Bacteriocin-Producing Bacteria Probiotics

4-1: Culture of Bacteriocin-Producing Bacteria

While Example 3 used the nisin A reagent, Example 4 used *Lactococcus lactis* FERM BP-8552 as the nisin Z-producing bacteria. The nisin Z-producing bacteria were cultured at 100 rpm at 30° C. in a medium (1 L of Lactobacilli MRS Broth manufactured by BD Difco) in a 5 L Sakaguchi flask. The culture was carried out for 20 hours as a standard, and the culture solution was prepared by measuring the optical density at a wavelength of 610 nm with a spectrophotometer (Biophoto-recorder TVS062CA manufactured by ADVANTEC) to be 0.1 or more when diluted 26 times.

In the same manner, subtilin and plantaricin cell fractions were obtained. Note that *Bacillus subtilis* ATCC 6633 was used as the subtilin-producing bacterium. *Lactobacillus plantarum* JCM 1057 was used as the plantaricin-producing bacterium.

4-2: Preparation of Bacteriocin-Producing Bacteria Powder

The cell fraction of nisin Z obtained in 4-1 was added to 120 ml of the protective agent, and dried by a spray dryer (inlet temperature 80° C. and outlet temperature 50° C.) or depressurized freeze-drying. The protective agent is as follows.
(A) skim milk 10% by mass (manufactured by BD)+sodium glutamate 3% by mass (MSG, AJICO)
(B) MSG 3% by mass, sorbitol 10% by mass, trehalose 10% by mass, and sucrose 10% by mass ((MSG was manufactured by AJICO, and the others except for MSG were manufactured by Wako Pure Chemical Industries, Ltd.)

The viable cell count in the obtained nisin Z-producing bacteria powder was measured. The viable cell count was measured as follows. The powder sample in an amount of 0.01 g was suspended in 1 ml of physiological saline, and the physiological saline was diluted 10 times in sequence, 0.1 ml of which was smeared on an MRS agar plate, and cultured at 30° C. for 24 hours, and the number of colonies formed was used to measure the colony formed unit (cfu)/g.

Similarly, subtilin- and plantaricin-producing bacteria powder was obtained, and the producing bacteria were measured.

4-3: Preparation of Coated-Nisin Z-Producing Bacteria Powder, Coated-Subtilin-Producing Bacteria Powder, and Coated-Plantaricin-Producing Bacteria Powder The nisin Z-producing bacteria powder prepared in 4-2 was coated in the same manner as described in 1-1 of Example 1 to obtain coated-nisin Z-producing bacteria powder.

Similarly, coated-subtilin-producing bacteria powder and coated-plantaricin-producing bacteria powder were prepared.

4-4: Acid Resistance and Enteric Test

The coated bacteriocin-producing bacteria powder obtained in 4-3 was subjected to the artificial gastric juice treatment and artificial intestinal juice treatment described in 1-2 of Examples 1.

The acid resistance was evaluated by measuring the viable cell count and antibacterial activity of each bacteriocin after artificial gastric juice treatment and artificial intestinal juice treatment. The viable cell count was measured according to the description in 4-2. The antibacterial activity was measured according to the description in B-2 of Experimental Example B. Table 11 presents the results. Note that the meanings of "+" and "ND" in the table are the same as those described in Table 10.

TABLE 11

| | Ctr 0 (hr) | | Gastric Juice Treatment 2 (hr) | | Intestinal Juice Treatment 4 (hr) | |
|---|---|---|---|---|---|---|
| Bacteriocin | Growth, cfu | Antibacterial Activity | Growth, cfu | Antibacterial Activity | Growth, cfu | Antibacterial Activity |
| Nisin Z | $2.1*10^{10}$ | ++++ | $1.4*10^{2}$ | ND | $1.0*10^{2}$ | ND |
| Subtilin | $2.1*10^{8}$ | ++++ | $1.1*10^{8}$ | ++ | $1.0*10^{8}$ | ++ |
| Plantaricin | $7.1*10^{10}$ | ++ | $2.0*10^{5}$ | ND | $2.0*10^{5}$ | ND |

4-5: Chicken Growth Test Using Coated-Nisin Z-Producing Bacteria Powder

The coated-nisin Z-producing bacteria powder prepared in 4-3 was added to the feed matrix presented in Table 2 so that the viable cell count was as in the table below, and the method described in 1-3 of Example 1 was followed to evaluate the body weight gain effect and feed conversion ratio of chickens.

TABLE 12

| | | 0-3 weeks | |
|---|---|---|---|
| Category | Amount Added (cfu) | BWG | FCR |
| Non Treatment | — | 100 | 100 |
| Nisin Producer | $10^{10}$ | 103 | 100 |

Example 5: Chicken Growth Test

Three conditions were prepared, a AGP-containing feed (PC) obtained by adding antibiotics (lasalocid 0.05% by mass and avilamycin 0.01% by mass) to a standard feed, a PRB-supplemented feed (nisin (Lc)) supplemented with 2% of nisin A culture solution obtained by culturing *Lactococcus lactis* NCIMB 8780 in the same manner as in Example 4-1, and a AGP-free feed (standard feed only) (NC), and were administered to newborn chicks. Note that, for one condition, ten Cobb Broiler male newborn chicks were used, and the experiment was repeated three times to evaluate the body weight gain effect and feed conversion ratio of chickens. For the drug-free group (NC), a standard feed (ME 3160 kcal and CP 22% by mass without antibiotics used) was used. For the PC and nisin addition group, 2% by mass of the antibiotics (lasalocid and avilamycin) or nisin Z-containing liquid was added to the standard feed (ME 3160 kcal and CP 22% by mass), respectively.

TABLE 13

| | BWG | | FCR | |
|---|---|---|---|---|
| Category | 1 w | 2 w | 1 W | 2 W |
| NC | 106.2 ± 3.0 | 330.3 ± 7.8 | 1.19 ± 1 | 1.34 ± 0.02 |
| PC* | 110.4 ± 4.7 | 379.9 ± 10.0 | 1.08 ± 0 | 1.23 ± 0.02 |
| Nisin (Lc)** | 111.1 ± 5.4 | 352.4 ± 27.9 | 1.23 ± 2 | 1.35 ± 0.03 |

*Antibiotics: lasalocid 0.05% and avilamycin 0.01% added.
**For nisin, 2% *Lactococcus lactis* culture solution was added.

What is claimed is:

1. A coated-type feed additive composition for improving body weight gain of livestock or feed conversion ratio for livestock comprising:
   (a) a core containing a physiologically active substance having a property of strengthening a membrane of intestinal epithelial cells; and
   (b) a core coating agent, which is capable of forming an enteric coating, wherein the physiologically active substance contains one or more bacteriocins, and wherein the coating agent is hydrogenated rapeseed oil and/or shellac.

2. A coated-type feed additive composition for improving body weight gain of livestock or feed conversion ratio for livestock according to claim 1, wherein
   the physiologically active substance is at least one bacteriocin selected from the group consisting of nisin, subtilin, plantaricin, and gassericin.

3. A coated-type feed additive composition for improving body weight gain of livestock or feed conversion ratio for livestock according to claim 2, wherein
   the physiologically active substance is a bacteriocin that is contained in a culture of a microorganism which produces the substance.

4. A coated-type feed additive composition for improving body weight gain of livestock or feed conversion ratio for livestock according to claim 2, wherein
   the physiologically active substance is a bacteriocin that is contained in a culture of at least one microorganism selected from the group consisting of *Bacillus, Lactococcus, Lactobacillus, Leuconostoc,* and *Pediococcus*.

5. A coated-type feed additive composition for improving body weight gain of livestock or feed conversion ratio for livestock according to claim 2, wherein
   the microorganism is *Bacillus subtilis, Lactococcus lactis* or *Lactobacillus plantarum*.

6. A coated-type feed additive composition for improving body weight gain of livestock or feed conversion ratio for livestock according to claim 1, comprising:
   (a) a core containing a physiologically active substance that is a bacteriocin having a property of strengthening a membrane of intestinal epithelial cells and that according to claim 1 wherein the physiologically active substance is selected from the group consisting of nisin, subtilin, plantaricin, and gassericin; and
   (b) a core coating agent, wherein
   the coating agent is capable of forming an enteric coating and contains at least one selected from the group consisting of hydrogenated vegetable oil, shellac, zein, hydroxypropyl methylcellulose, and maltitol.

7. A coated-type feed additive composition for improving body weight gain of livestock or feed conversion ratio for livestock according to claim 6, wherein the coating layer formed by the coating agent has a two-layer structure including a layer formed of hydrogenated rapeseed oil and a layer formed of shellac.

8. A coated-type feed additive composition for improving body weight gain of livestock or feed conversion ratio for livestock according to claim 7, wherein
   the layer formed of shellac is in contact with the core, and the layer formed of hydrogenated rapeseed oil is formed thereon.

9. A feed comprising:
the coated-type feed additive composition for improving body weight gain of livestock or feed conversion ratio for livestock according to claim 1.

10. A method of improving a body weight gain of livestock and feed conversion ratio for livestock, comprising: administering to the livestock a feed comprising an antibacterially effective amount of the coated-type feed additive composition according to claim 1.

11. The method according to claim 10, wherein
the physiologically active substance is at least one bacteriocin selected from the group consisting of raisin, subtilin, plantaricin, and gassericin.

12. The method according to claim 10, wherein
the physiologically active substance is contained as a culture of a microorganism which produces the substance.

13. The method according to claim 10, wherein the physiologically active substance is contained as a culture of at least one microorganism selected from the group of genera consisting of *Bacillus, Lactococcus, Lactobacillus, Leuconostoc*, and *Pediococcus*.

14. The method according to claim 13, wherein the microorganism is *Bacillus subtilis, Lactococcus lactis*, or *Lactobacillus plantarum*.

15. A coated-type feed additive composition for improving body weight gain of livestock or feed conversion ratio for livestock according to claim 1, wherein the composition is fed to monogastric animals.

\* \* \* \* \*